(12) United States Patent
Fukazawa et al.

(10) Patent No.: US 8,367,846 B2
(45) Date of Patent: Feb. 5, 2013

(54) METHOD OF PRODUCING 2-ALKYL-3-AMINOTHIOPHENE DERIVATIVE

(75) Inventors: Yasuaki Fukazawa, Mobara (JP); Yoji Aoki, Chiba (JP); Haruko Mita, Omuta (JP); Hironori Komatsu, Kurume (JP)

(73) Assignee: Mitsui Chemicals Agro, Inc., Minato-Ku, Tokyo (JP)

( * ) Notice: Subject to any disclaimer, the term of this patent is extended or adjusted under 35 U.S.C. 154(b) by 130 days.

(21) Appl. No.: 12/762,083

(22) Filed: Apr. 16, 2010

(65) Prior Publication Data
US 2010/0267963 A1  Oct. 21, 2010

Related U.S. Application Data

(60) Provisional application No. 61/170,183, filed on Apr. 17, 2009.

(51) Int. Cl.
*C07D 231/00* (2006.01)
(52) U.S. Cl. ............ 548/365.7; 564/509; 564/504; 564/510; 564/503; 549/68
(58) Field of Classification Search ........... 548/365.7; 564/509, 504, 510, 503; 549/68
See application file for complete search history.

(56) References Cited

U.S. PATENT DOCUMENTS
2,545,433 A * 3/1951 Grob ..................... 549/63

FOREIGN PATENT DOCUMENTS
JP  2008-120710 A  5/2008

OTHER PUBLICATIONS

Kellogg et al. (J. Org. Chem. (1971), 36 (16), 2236-2244).*
Scott et al. (J. Org. Chem. (1964), 29 (8), 2165-2168.*
Justus Liebigs Annalen der Chemie, vol. 501, (1933), p. 174 (w/English Abstract).
Gamal Guiglio-Tonolo et al., Original reaction of *p*-nitrobenzyl chloride with aldehydes using tetrakis(dimethylamino)ethylene TDAE), Tetrahedron Letters 44 (2003) 6433-6435.

* cited by examiner

*Primary Examiner* — Andrew D Kosar
*Assistant Examiner* — Valerie Rodriguez-Garcia
(74) *Attorney, Agent, or Firm* — Buchanan Ingersoll & Rooney PC

(57) ABSTRACT

The present invention provides a method of producing 2-alkyl-3-aminothiophene derivative represented by Formula (4), the method comprising oxidizing a compound represented by the following Formula (1) to produce a compound represented by the following Formula (3) and reducing the compound represented by the following Formula (3):

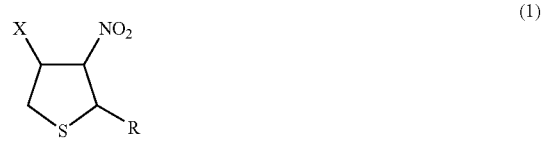

(1)

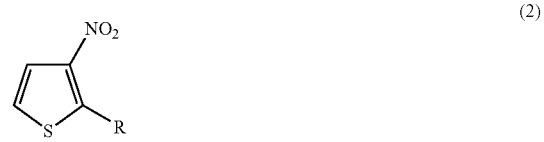

(2)

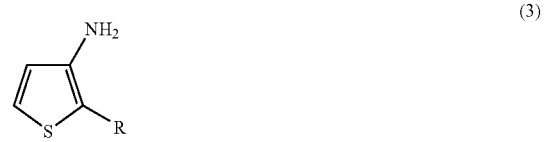

(3)

wherein in Formula (1), Formula (3), and Formula (4), R represents an alkyl group, a cycloalkyl group, or a bicycloalkyl group; and X represents a hydroxyl group, a halogen atom acyloxy group, an alkylsulfonyl group, or an arylsulfonyl group.

19 Claims, No Drawings

METHOD OF PRODUCING 2-ALKYL-3-AMINOTHIOPHENE DERIVATIVE

CROSS-REFERENCE TO RELATED APPLICATIONS

This application claims priority under 35 U.S.C. 119(e) to Provisional U.S. Patent Application No. 61/170,183, filed Apr. 17, 2009, the disclosure of which is incorporated by reference herein.

BACKGROUND OF THE INVENTION

1. Field of the Invention

The present invention relates to a method of producing 2-alkyl-3-aminothiophne, and intermediates for producing the same.

2. Description of the Related Art

As a method of producing 2-alkyl-3-aminothiophene, a method of reacting a 3-aminothiophene derivative with a carbonyl compound to produce a 2-alkenyl-3-aminothiophene derivative, and then reducing the same, is disclosed (for example, refer to Japanese Patent Application Laid-Open (JP-A) No. 2008-120710).

Further, as a method of producing 2-alkyl-3-mitrothiophene, a method of reacting 3-nitrothiophene with a Grignard reagent, and then oxidizing the same, is disclosed (for examples, refer to Tetrahedron, Vol. 44, No. 20, (1988), p. 6435).

Moreover, as a method of producing 3-nitrothiophene, a method of nitrating thiophene is disclosed (for example, refer to Justus Liebigs Annalen der Chemie, Vol. 501, (1933), p. 174).

However, due to the instable nature of a 3-aminothiophene derivative and the difficulty in handling the same, the method described in Japanese Patent Application Laid-Open (JP-A) No. 2008-120710 requires a process of attaching/removing a protective group for the amino group, such as an acyl group or a carbamate group. Therefore, the method is still to be improved in terms of operability and cost efficiency.

On the other hand, since it is known that a nitro group can be converted to an amino group through a reduction reaction, as represented by catalytic hydrogenation, it is expected that a 3-amino-2-allylthiophene derivative can be produced by reducing a 2-alkyl-3-nitrothiophene derivative. However, due to the difficulty in producing the 3-alkyl-2-nitrothiophene derivative, no reports have been made concerning the method of producing a 2-alkyl-3-aminothiophene derivative by reducing a 2-alkyl-3-nitrothiophene derivative.

In the method of producing 2-alkyl-3-nitrothiophene described in Tetrahedron, Vol. 44, No. 20, (1988), p. 6435, there is room for improvement in that the production of 3-nitrothiophene, which is a starting material used in this method, is difficult.

In the method described in Justus Liebigs Annalen der Chemie, Vol. 501, (1933), p. 174, the yield of the resulting product is low since it is obtained as a mixture of position isomers, and a process of separating these isomers is necessary. Therefore, the method is still to be improved in terms of operability and cost efficiency.

SUMMARY OF THE INVENTION

The invention provides a method of producing 2-alkyl-3-aminothiophene in an efficient manner.

Namely, the invention provides a method of producing a 2-alkyl-3-aminothiophene derivative represented by the following Formula (4), the method including oxidizing a compound represented by the following Formula (1) to produce a compound represented by the following Formula (3) and reducing the compound represented by the following Formula (3):

(1)

in Formula (1), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms; and X representing a halogen atom or a substituent represented by the following Formula (2):

(2)

in Formula (2), A representing a carbon atom or a sulfur atom; n being 1 when A is a carbon atom, and being 1 or 2 when A is a sulfur atom, Q representing an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms, and # representing a site of bonding with the compound represented by Formula (1):

(3)

in Formula (3), R being the same as in Formula (1):

(4)

in Formula (4), R being the same as in Formula (1).

In the compound represented by Formula (1), R preferably represents a substituent represented by the following Formula (6):

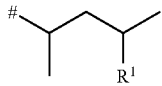
(6)

in Formula (6), $R^1$ representing a hydrogen atom, or a straight-chain or branched alkyl group having 1 to 6 carbon atoms and # representing a site of bonding with the compound represented by Formula (1).

In the compound represented by Formula (1), R represents a 1,3-dimethylbutyl group more preferably.

The method preferably further includes reacting a compound represented by the following Formula (8) with a halogenating agent or an esterifying agent to produce a compound represented by the following Formula (1a) and oxidizing the compound represented by the following Formula (1a) to produce the compound represented by Formula (3):

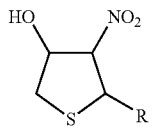
(8)

in Formula (8), R being the same as in Formula (1):

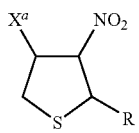
(1a)

in Formula (1a), R being the same as in Formula (1) and $X^a$ representing a halogen atom or the substituent represented by Formula (2).

The method preferably further includes producing a compound represented by the following Formula (5) from the compound represented by Formula (1) and oxidizing the compound represented by Formula (5) to produce the compound represented by Formula (3):

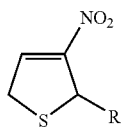
(5)

in Formula (5), R being the same as in Formula (1).

The method preferably further includes reacting a compound represented by the following Formula (7) with α-mercaptoacetaldehyde or 1,4-dithian-2,5-diol to produce a compound represented by the following Formula (8):

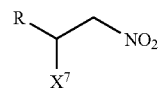
(7)

in Formula (7), R being the same as in Formula (1) and $X^7$ representing a halogen atom or a substituent represented by Formula (2)

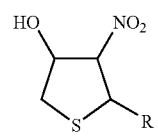
(8)

in Formula (8), R being the same as in Formula (1).

The compound represented by Formula (7) is preferably produced by a method further including reacting a compound represented by the following Formula (9) with a halogenating agent or an esterifying agent:

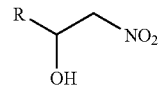
(9)

in Formula (9), R being the same as in Formula (1).

The compound represented by Formula (9) is preferably produced by a method further including reacting a compound represented by the following Formula (10) with nitromethane:

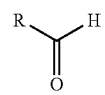
(10)

in Formula (10), R being the same as in Formula (1).

The method preferably further includes reacting a compound represented by the following Formula (11) with α-mercaptoacetaldehyde or 1,4-dithian-2,5-diol to produce a compound represented by the following Formula (8):

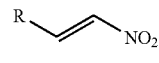
(11)

in Formula (11), R being the same as in Formula (1):

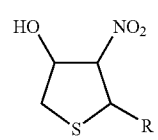
(8)

in Formula (8), R being the same as in Formula (1).

The compound represented by Formula (11) is preferably produced by a method further including dehydrating a compound represented by the following Formula (9):

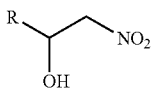
(9)

in Formula (9), R being the same as in Formula (1).

The compound represented by Formula (9) is preferably produced by a method further including reacting a compound represented by the following Formula (10) with nitromethane:

(10)

in Formula (10), R being the same as in Formula (1).

The invention further provides a hydroxynitroalkane derivative represented by the following Formula (9):

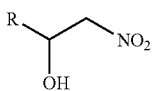
(9)

in Formula (9), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

The invention further provides a nitroalkane derivative represented by the following Formula (7):

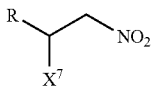
(7)

in Formula (7), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms; and $X^7$ representing a halogen atom or a substituent represented by the following Formula (2):

(2)

in Formula (2), A representing a carbon atom or a sulfur atom; n being 1 when A is a carbon atom, and being 1 or 2 when A is a sulfur atom; and Q representing an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms.

The invention further provides a nitroolefin derivative represented by the following Formula (11):

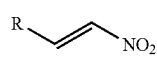
(11)

in Formula (11), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

The invention further provides a 3-hydroxy-4-nitrotetrahydrothiophene derivative represented by the following Formula (8):

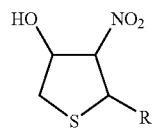
(8)

in Formula (8), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

The invention further provides a 3-nitrotetrahydrothiophene derivative represented by the following Formula (1):

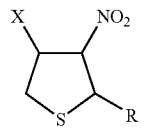
(1)

in Formula (1), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms; and X representing a hydroxy group, a halogen atom, or a substituent represented by the following Formula (2):

in Formula (2), A representing a carbon atom or a sulfur atom; n being 1 when A is a carbon atom, and being 1 or 2 when A is a sulfur atom; and Q representing an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms.

The invention further provides a 3-nitro-2,5-dihydrothiophene derivative represented by the following Formula (5):

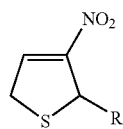

in Formula (5), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

The invention provides a 2-alkyl-3-nitrothiophene derivative represented by the following Formula (3):

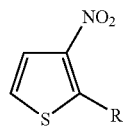

in Formula (3), R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

In the invention, in the hydroxynitroalkane derivative represented by Formula (9), the nitroalkane derivative represented by Formula (7), the nitroolefin derivative represented by Formula (11), the 3-hydroxy-4-nitrotetrahydrothiophene derivative represented by Formula (8), the 3-nitrotetrahydrothiophene derivative represented by Formula (1), the 3-nitro-2,5-dihydrothiophene derivative represented by Formula (5), and the 3-nitrothiophene derivative represented by Formula (3), R preferably represents a substituent represented by the following Formula (6) and more preferably represents a 1,3-dimethylbutyl group:

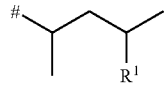

in Formula (6), $R^1$ representing a hydrogen atom, or a straight-chain or branched alkyl group having 1 to 6 carbon atoms and # representing a site of bonding with the 3-nitrotetrahydrothiophene derivative.

The invention further provides use of a compound represented by Formula (9), Formula (7), Formula (11), Formula (8), Formula (1), Formula (5), or Formula (3), as an intermediate for producing agricultural or medical products.

In the use of the compound, an antibacterial agent for agricultural and horticultural purposes represented by the following Formula (12) is preferably produced by the intermediate:

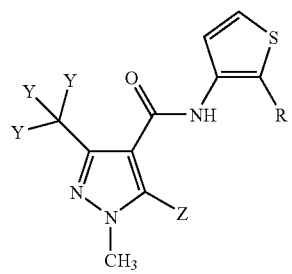

in Formula (12), each of Y and Z independently representing a halogen atom or a hydrogen atom, and R representing an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

In Formula (12), R preferably represents a substituent represented by the following Formula (6):

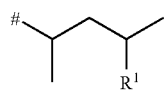

in Formula (6), $R^1$ representing a hydrogen atom, or a straight-chain or branched alkyl group having 1 to 6 carbon atoms and # representing a site to be bonded with the antibacterial agent.

In Formula (12), R represents a 1,3-dimethylbutyl group, Y represents a fluorine atom, and Z represents a hydrogen atom, more preferably.

DETAILED DESCRIPTION OF THE INVENTION

In the present invention, the term "process" is not only used for discrete process, but also for a process that is indistinguishable from other processes, so long as the intended purpose or results can be accomplished or obtained.

In the following, the invention is described in further detail.

In the invention, in the aldehyde represented by Formula (10), the hydroxynitroalkane represented by Formula (9), the nitroolefin represented by Formula (11), the nitroalkane represented by Formula (7), the 3-hydroxy-4-nitrotetrahydrothiophene represented by Formula (8), the 3-nitro-2,5-dihydrothiophene represented by Formula (5), the 2-alkyl-3-nitrothiophene represented by Formula (3), the 2-alkyl-3-aminothiophene represented by Formula (4) and the 3-nitrotetrahydrothiophene represented by Formula (1), examples of R, which represents an alkyl group having 1 to 18 carbon atoms that may be substituted by alkyl groups having 1 to 10 carbon atoms or by cycloalkyl groups having 3 to 10 carbon atoms; a cycloalkyl group having 3 to 10 carbon atoms that may be substituted by alkyl groups having 1 to 10 carbon atoms or by cycloalkyl groups having 3 to 10 carbon atoms; or a bicycloalkyl group having 6 to 12 carbon atoms that may be substituted by alkyl groups having 1 to 10 carbon atoms or by cycloalkyl groups having 3 to 10 carbon atoms, include the following:

a methyl group, an ethyl group, a propyl group, a butyl group, a pentyl group, a hexyl group, an isopropyl group, an isobutyl group, a secondary butyl group, a tertiary butyl group, a 1-methylbutyl group, a 2-methylbutyl group, a 3-methylbutyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclopropylmethyl group, a cyclopentylmethyl group, a cyclohexylethyl group, a cyclopropyl group, a cyclobutyl group, a cyclopentyl group, a cyclohexyl group, a methylcyclohexyl group, a cyclohexylcyclohexyl group, a hexahydroindan-1-yl group, a hexahydroindan-2-yl group, a hexahydroindan-4-yl group, a hexahydroindan-5-yl group, a decahydronaphthalen-1-yl group, and a decahydronaphthalene-2-yl group.

Further, in Formula (2), examples of Q that represents an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms include the following:

a methyl group, an ethyl group, a propyl group, a butyl group, a pentyl group, a hexyl group, an isopropyl group, an isobutyl group, a secondary butyl group, a tertiary butyl group, a 1-methylbutyl group, a 2-methylbutyl group, a 3-methylbutyl group, a 1,1-dimethylpropyl group, a 2,2-dimethylpropyl group, a 1,2-dimethylpropyl group, a 1-methylpentyl group, a 2-methylpentyl group, a 3-methylpentyl group, a 4-methylpentyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a cyclopropyl group, a cyclobutyl group, a cyclopentyl group, a cyclohexyl group, a trifluoromethyl group, a 2,2,2-trifluoroethyl group, a methoxy group, an ethoxy group, a tertiary butyloxy group, a benzyloxy group, a phenyl group, a naphthyl group, a 2-methylphenyl group, a 3-methylphenyl group, and a 4-methylphenyl group.

If there are diastereomers in the aldehyde represented by Formula (10), the hydroxynitroalkane represented by Formula (9), the nitroolefin represented by Formula (11), the nitroalkane represented by Formula (7), the 3-hydroxy-4-nitrotetrahydrothiophene represented by Formula (8), the 3-nitro-2,5-dihydrothiophene represented by Formula (5), the 2-alkyl-3-nitrothiophene represented by Formula (3), the 2-alkyl-3-aminothiophene represented by Formula (4) and the 3-nitro tetrahydrothiophene represented by Formula (1), the compounds may consist only of one kind of diastereomer, or two or more kinds of diastereomer may be included at arbitrary ratios, and the structures of the compounds are not particularly limited.

If there are enantiomers in the aldehyde represented by Formula (10), the hydroxynitroalkane represented by Formula (9), the nitroolefin represented by Formula (11), the nitroalkane represented by Formula (7), the 3-hydroxy-4-nitrotetrahydrothiophene represented by Formula (8), the 3-nitro-2,5-dihydrothiophene represented by Formula (5), the 2-alkyl-3-nitrothiophene represented by Formula (3), the 2-alkyl-3-aminothiophene represented by Formula (4) and the 3-nitro tetrahydrothiophene represented by Formula (1), the compounds may consist only of one kind of enantiomer, or may be a mixture including both enantiomers at arbitrary ratios, and the structures thereof are not particularly limited.

The nitroolefin represented by Formula (11) may consist only of cis-isomers or trans-isomers, or both of these may be included at arbitrary ratios, and the structures thereof are not particularly limited.

Many of the aldehydes represented by Formula (10) used as a starting compound in the invention are available as commercial products, and some that are difficult to obtain can be produced by various known methods, such as a method described in Journal of American Chemical Society, Vol. 75, No. 20, (1953), p. 4995.

According to a novel method disclosed by the invention, the hydroxynitroalkane represented by Formula (9) can be produced by reacting the aldehyde represented by Formula (10) with nitromethane in the presence of a base.

The amounts of the nitromethane and the base with respect to the aldehyde represented by Formula (10) are not particularly limited, but are preferably three equivalents or less, respectively, from an economic viewpoint.

The base to be used may be an inorganic base or an organic base. Exemplary inorganic bases include hydroxides of an alkali metal, hydroxides of an alkaline earth metal, carbonates of an alkali metal, and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

A solvent may be used in the method of producing the hydroxynitroalkane represented by Formula (9), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the aldehyde represented by Formula (10), from an economic viewpoint.

The reaction temperature is not particularly limited, but is preferably not less than the melting point of the solvent but not more than the boiling point of the same, in view of operation efficiency.

In the invention, the method of producing the hydroxynitroalkane represented by Formula (9) may include further processes, such as a post treatment, as necessary.

According to a novel method disclosed by the invention, the nitroolefin represented by Formula (11) can be produced by subjecting the hydroxynitroalkane represented by Formula (9) to a dehydration reaction.

An acid may be used to aid the reaction in the method of producing the nitroolefin represented by Formula (11). The acid may be an inorganic acid or an organic acid, and may be a Brønsted acid or a Lewis acid.

Specific examples of the acid include sulfuric acid, fuming sulfuric acid, chlorosulfuric acid, nitric acid, fuming nitric acid, hydrochloric acid, phosphoric acid, hydrogen bromide, acetic acid, trifluoroacetic acid, oxalic acid, tartaric acid, fumaric acid, maleic acid, benzoic acid, methanesulfonic acid, benzenesulfonic acid, p-toluenesulfonic acid, trifluoromethanesulfonic acid, aluminum chloride, titanium tetrachloride and boron trifluoride etherate. These acids may be used alone, or two or more kinds thereof may be combined at arbitrary ratios.

A base may be used to aid the reaction in the method of producing the nitroolefin represented by Formula (11). The base to be used may be an inorganic base or an organic base. Exemplary inorganic bases include hydroxides of an alkali metal, hydroxides of an alkaline earth metal, carbonates of an alkali metal, and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

A known dehydrating agent may be used to aid the reaction in the method of producing the nitroolefin represented by Formula (11).

Examples of the dehydrating agent to be used include carboxylic halides such as acetyl chloride and benzoyl chloride, carboxylic anhydrides such as acetic anhydride and trifluoroacetic anhydride, sulfonic halides such as toluenesulfonyl chloride, methanesulfonyl chloride and trifluoromethanesulfonyl chloride, thionyl chloride, sulfuryl chloride, oxalyl chloride, phosgene, diphosgene, triphosgene, phosphorus pentachloride, phosphorus trichloride, phosphorus oxychloride, phosphorus tribromide, phosphorus pentaoxide, alkali metal sulfates, alkaline earth metal sulfates and alkaline earth metal hydrochlorides. These dehydrating agents may be used alone, or two or more kinds thereof may be combined at arbitrary ratios.

A solvent may be used in the method of producing the nitroolefin represented by Formula (11), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the hydroxynitroalkane represented by Formula (9), from an economic viewpoint.

The reaction temperature is not particularly limited, but is preferably not less than the melting point of the solvent but not more than the boiling point of the same, in view of operation efficiency.

In the invention, the method of producing the nitroolefin represented by Formula (11) may include further processes, such as a post treatment, as necessary.

According to a novel method disclosed by the invention, the nitroalkane represented by Formula (7) can be produced by reacting the hydroxynitroalkane represented by Formula (9) with a known esterifying agent or a halogenating agent.

Examples of the $X^7$ in the nitroalkane represented by Formula (7) include a fluorine atom, a chlorine atom, a bromine atom, an iodine atom, an acetoxy group, a trifluoroacetoxy group, a methanesulfonyloxy group, a trifluoromethanesulfonyloxy group, a p-toluenesulfonyloxy group, a benzoxycarbonyloxy group, a tertiary butoxycarbonyloxy group and a benzoyloxy group.

A base may be used to aid the reaction in the method of producing the nitroalkane represented by Formula (7). The base to be used may be an inorganic base or an organic base. Exemplary inorganic bases include hydroxides of an alkali metal, hydroxides of an alkaline earth metal, carbonates of an alkali metal, and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

Examples of the esterifying agent or the halogenating agent to be used in the method of producing the nitroalkane represented by Formula (7) include carboxylic halides such as acetyl chloride and benzoyl chloride, carboxylic anhydrides such as acetic anhydride and trifluoroacetic anhydride, sulfonic halides such as toluenesulfonyl chloride, methanesulfonyl chloride and trifluoromethanesulfonyl chloride, thionyl chloride, sulfuryl chloride, oxalyl chloride, phosgene, diphosgene, triphosgene, phosphorus pentachloride, phosphorus trichloride, phosphorus oxychloride and phosphorus tribromide. These esterifying agent or the halogenating agent may be used alone, or two or more kinds thereof may be combined at arbitrary ratios.

A solvent may be used in the method of producing the nitroalkane represented by Formula (7), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the hydroxynitroalkane represented by Formula (9), from an economic viewpoint.

The reaction temperature is not particularly limited, but is preferably not less than the melting point of the solvent but not more than the boiling point of the same, in view of operation efficiency.

In the invention, the method of producing the nitroalkane represented by Formula (4) may include further processes, such as a post treatment, as necessary.

According to a novel method disclosed by the invention, the 3-hydroxy-4-nitrotetrahydrothiophene represented by Formula (8) can be produced by reacting the nitroolefin represented by Formula (11) or the nitroalkane represented by Formula (7) with α-mercaptoacetaldehyde or 1,4-dithian-2,5-diol.

In the reaction, the amount of α-mercaptoacetaldehyde or 1,4-dithian-2,5-diol with respect to the amount of the nitroolefin represented by Formula (11) or the nitroalkane represented by Formula (7) is not particularly limited, but is preferably three equivalents or less (in terms of α-mercaptoaldehyde) from an economic viewpoint. The α-mercaptoacetaldehyde can be used in the form of a monomer, but is more suitably used in the form of a dimer, i.e., 1,4-dithian-2,5-diol, which can be obtained as a commercial product.

A base may be used to aid the reaction in the method of producing 3-hydroxy-4-nitrotetrahydrothiophene represented by Formula (8). The base to be used may be an inorganic base or an organic base. Exemplary inorganic bases include hydroxides of an alkali metal, hydroxides of an alkaline earth metal, carbonates of an alkali metal and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

A solvent may be used in the method of producing the 3-hydroxy-4-nitrotetrahydrothiophene represented by Formula (8), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the nitroolefin represented by Formula (11) or the nitroalkane represented by Formula (7), from an economic viewpoint.

The reaction temperature is not particularly limited, but is preferably not less than the melting point of the solvent but not more than the boiling point of the same, in view of operation efficiency.

In the invention, the method of producing the 3-hydroxy-4-nitrotetrahydrothiophene represented by Formula (8) may include further processes, such as a post treatment, as necessary.

According to a novel method disclosed by the invention, the 3-nitro-2,5-dihydrothiophene represented by Formula (5) can be produced by subjecting the 3-hydroxy-4-nitrotetrahydrothiophene represented by Formula (8) to a dehydration reaction.

An acid may be used to aid the reaction in the method of producing the 3-nitro-2,5-dihydrothiophene represented by Formula (5). The acid may be an inorganic acid or an organic acid, and may be a Brønsted acid or a Lewis acid.

Specific examples of the acid include sulfuric acid, fuming sulfuric acid, chloro sulfuric acid, nitric acid, fuming nitric acid, hydrochloric acid, phosphoric acid, hydrogen bromide, acetic acid, trifluoro acetic acid, oxalic acid, tartaric acid, fumaric acid, maleic acid, benzoic acid, methane sulfonic acid, benzene sulfonic acid, tosic acid, trifluoromethane sulfonic acid, aluminum chloride, titanium tetrachloride and boron trifluoride etherate. These acids may be used alone, or two or more kinds thereof may be combined at arbitrary ratios.

A base may be used to aid the reaction in the method of producing the 3-nitro-2,5-dihydrothiophene represented by Formula (5). The base to be used may be an inorganic base or an organic base. Exemplary inorganic bases include hydroxides of an alkali metal, hydroxides of an alkaline earth metal, carbonates of an alkali metal, and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

A known dehydrating agent may be used to aid the reaction in the method of producing the 3-nitro-2,5-dihydrothiophene represented by Formula (5).

Examples of the dehydrating agent to be used include carboxylic halides such as acetyl chloride and benzoyl chloride, carboxylic anhydrides such as acetic anhydride and trifluoroacetic anhydride, sulfonic halides such as toluenesulfonyl chloride, methanesulfonyl chloride and trifluoromethanesulfonyl chloride, thionyl chloride, sulfuryl chloride, oxalyl chloride, phosgene, diphosgene, triphosgene, phosphorus pentachloride, phosphorus trichloride, phosphorus oxychloride, phosphorus tribromide, phosphorus pentaoxide, alkali metal sulfates, alkaline earth metal sulfates and alkaline earth metal hydrochlorides. These dehydrating agents may be used alone, or two or more kinds thereof may be combined at arbitrary ratios.

A solvent may be used in the method of producing the 3-nitro-2,5-dihydrothiophene represented by Formula (5), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the 3-hydroxy-4-nitrotetrahydrothiophene represented by Formula (8), from an economic viewpoint.

The reaction temperature is not particularly limited, but is preferably not less than the melting point of the solvent but not more than the boiling point of the same, in view of operation efficiency.

In the invention, the method of producing the 3-nitro-2,5-dihydrothiophene represented by Formula (5) may include further processes, such as a post treatment, as necessary.

According to a novel method disclosed by the invention, the 3-nitrotetrahydrothiophene derivative represented by Formula (1a) can be produced by reacting the 3-hydroxy-4-nitrotetrahydrothiophene represented by Formula (8) with a known esterifying agent or a halogenating agent.

A base may be used to aid the reaction in the method of producing the 3-nitrotetrahydrothiophene derivative represented by Formula (1a). The base to be used may be an inorganic base or an organic base. Exemplary inorganic bases include hydroxides of an alkali metal, hydroxides of an alkaline earth metal, carbonates of an alkali metal, and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

Examples of the esterifying agent or the halogenating agent to be used in the method of producing the 3-nitrotetrahydrothiophene derivative represented by Formula (1a) include carboxylic halides such as acetyl chloride and benzoyl chloride, carboxylic anhydrides such as acetic anhydride and trifluoroacetic anhydride, sulfonic halides such as toluenesulfonyl chloride, methanesulfonyl chloride and trifluoromethanesulfonyl chloride, thionyl chloride, sulfuryl chloride, oxalyl chloride, phosgene, diphosgene, triphosgene, phosphorus pentachloride, phosphorus trichloride, phosphorus oxychloride and phosphorus tribromide. These esterifying agent or the halogenating agent may be used alone, or two or more kinds thereof may be combined at arbitrary ratios.

A solvent may be used in the method of producing the 3-nitrotetrahydrothiophene derivative represented by Formula (1a), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the 3-hydroxy-4-nitrotetrahydrothiophene represented by Formula (8), from an economic viewpoint.

The reaction temperature is not particularly limited, but is preferably not less than the melting point of the solvent but not more than the boiling point of the same, in view of operation efficiency.

In the invention, the method of producing the 3-nitrotetrahydrothiophene derivative represented by Formula (1a) may include further processes, such as a post treatment, as necessary.

According to a novel method disclosed by the invention, the 2-alkyl-3-nitrothiophene derivative represented by Formula (3) can be produced by oxidizing the 3-nitro-2,5-dihydrothiophene represented by Formula (5) or the 3-nitrotetrahydrothiophene derivative represented by Formula (1a) using an oxidizing agent.

Examples of the oxidizing agent used in the method of producing the 2-alkyl-3-nitrothiophene derivative represented by Formula (3) of the invention include a manganese compound, chromic acids, lead tetrachloride, osmium tetrachloride, ruthenium tetrachloride, chlorine, bromine, iodine, hypochlorous acid and a salt thereof, chloric acid and a salt thereof, bromic acid and a salt thereof, oxygen, ozone, hydrogen peroxide, organic peroxides, organic peracids, sulfuryl chloride, thionyl chloride, oxalyl chloride, phosgene, diphosgene and triphosgene. Among these, chlorine and sulfuryl chloride are preferably used.

A base may be used to aid the reaction in the method of producing the 2-alkyl-3-nitrothiophene represented by Formula (3). The base to be used may be an inorganic base or an organic base. Exemplary inorganic bases include hydroxides of an alkali metal, hydroxides of an alkaline earth metal, carbonates of an alkali metal and ammonias. Exemplary organic bases include trialkylamine and pyridines. Specific examples of the base include lithium hydroxide, sodium hydroxide, potassium hydroxide, calcium hydroxide, barium hydroxide, sodium carbonate, potassium carbonate, sodium hydrogen carbonate, potassium hydrogen carbonate, liquid ammonia, aqueous ammonia, triethylamine, tributylamine, pyridine, collidine, 2,6-lutidine and 4-dimethylaminopyridine. These bases may be used alone, or two or more kinds thereof may be combined at arbitrary ratios.

A solvent may be used in the method of producing the 2-alkyl-3-nitrothiophene represented by Formula (3), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the 3-nitro-2,5-dihydrothiophene represented by Formula (5) or the 3-nitrotetrahydrothiophene derivative represented by Formula (1a) from an economic viewpoint.

The reaction temperature is not particularly limited, but is preferably not less than the melting point of the solvent but not more than the boiling point of the same, in view of operation efficiency.

In the invention, the method of producing the 2-alkyl-3-nitrothiophene represented by Formula (3) may include further processes, such as a post treatment, as necessary.

According to a novel method disclosed by the invention, the 2-alkyl-3-aminothiophene derivative represented by Formula (4) can be produced by reducing the 2-alkyl-3-nitrothiophene derivative represented by Formula (3).

Examples of the reduction method used in the method of producing the 2-alkyl-3-aminothiophene derivative represented by Formula (4) include a method of performing catalytic hydrogenation; a method of using an alkali metal in a liquid ammonia; a method of using a metal such as iron, zinc, aluminum or tin; a method of using a metal salt such as tin chloride (II); and a method of using a metal hydride complex such as sodium borohydride or lithium aluminum hydride. Among these, a method of performing catalytic hydrogenation, a method of using iron and a method of using tin chloride (II) are preferably used.

A solvent may be used in the method of producing the 2-alkyl-3-aminothiophene derivative represented by Formula (4), but the solvent is not particularly limited. Examples of the solvent include alkyl halides such as dichloromethane and chloroform, aromatic hydrocarbons such as benzene, toluene and xylene, hydrocarbons such as hexane, heptane and cyclohexane, ethers such as diethylether, diisopropylether, 1,2-dimethoxyethane, tetrahydrofuran and dioxane, esters such as ethyl acetate and butyl acetate, amides such as N,N-dimethylformamide, N,N-dimethylacetamide and N-methylpyrrolidone, N,N'-dimethylimidazolidinone, acetonitrile, and water. These solvents may be used alone, or two or more kinds thereof may be combined at arbitrary ratios.

The amount of the solvent used for the reaction is not particularly limited, but is preferably not more than 50 times the weight of the 2-alkyl-3-nitrothiophene derivative represented by Formula (3), from an economic viewpoint.

The reaction temperature is not particularly limited, but is preferably not less than the melting point of the solvent but not more than the boiling point of the same, in view of operation efficiency.

In the invention, the method of producing the 2-alkyl-3-aminothiophene represented by Formula (4) may include further processes, such as a post treatment, as necessary.

The 2-alkyl-3-aminothiophene obtained by the method of producing the 2-alkyl-3-aminothiophene according to the invention can be used as an intermediate for producing antibacterial agents for agricultural and horticultural purposes; an intermediate for producing insecticides for agricultural and horticultural purposes; an intermediate for producing herbicides for agricultural and horticultural purposes; or an intermediate for producing medical products. For example, the compound is useful as an intermediate for the antibacterial agent for agricultural and horticultural purposes as described in JP-A No. 09-235282.

EXAMPLES

In the following, the present invention will be described in more detail with reference to examples, but the present invention is not limited thereto.

Example 1-1

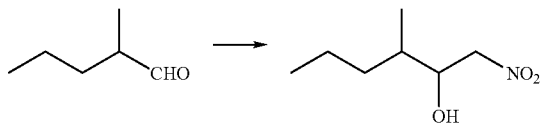

After dissolving 7.0 g of sodium hydroxide in 50 ml of water and 50 ml of ethanol at 4° C., 10.7 g of nitromethane and 10.0 g of 2-methylpentanal were added thereto. The temperature of the solution was allowed to rise to room temperature, and the solution was stirred for two hours. After concentrating the ethanol under reduced pressure, the solution was neutralized with 1 mol/l of hydrochloric acid so that the pH of the solution was approximately 7. Ethyl acetate was added to the solution, and the organic layer was washed with saturated saline. The organic layer was dried with magnesium sulfate and concentrated, and then purified by silica gel chromatography (hexane/ethyl acetate=8/1), thereby obtaining 13.3 g of 3-methyl-1-nitro-2-hexanol (yield: 94.2%).

$^1$H-NMR (CDCl$_3$): δ=0.90-0.96 (6H, m), 1.18-1.47 (4H, m), 1.62 (1H, m), 4.15 (1H, m), 4.39 (2H, m).

Example 1-2

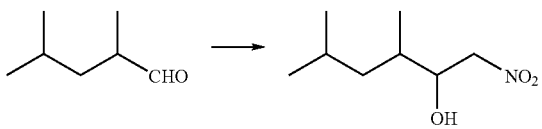

After dissolving 5.0 g of sodium hydroxide in 25 ml of water and 25 ml of ethanol at 4° C., 7.7 g of nitromethane and 7.2 g of 2,5-dimethylpentanal were added thereto. The temperature of the solution was allowed to rise to room temperature, and the solution was stirred for an hour. After concentrating the ethanol under reduced pressure, the solution was neutralized with 1 mol/l of hydrochloric acid so that the pH of the solution was approximately 7. Ethyl acetate was added to the solution, and the organic layer was washed with saturated saline. The organic layer was dried with magnesium sulfate and concentrated, and then purified by silica gel chromatography (hexane/ethyl acetate=8/1), thereby obtaining 9.0 g of 3,5-dimethyl-1-nitro-2-hexanol (yield: 81.4%).

$^1$H-NMR (CDCl$_3$): δ=0.85-0.95 (9H, m), 1.12-1.28 (2H, m), 1.64-1.69 (2H, m), 4.22-4.24 (1H, m), 4.44-4.46 (2H, m).

Example 2-1

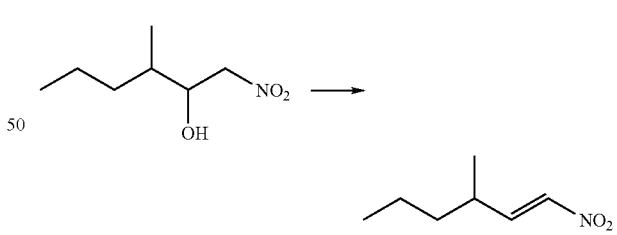

After dissolving 15.0 g of 3-methyl-1-nitro-2-hexanol in 100 ml of dichloromethane, 11.7 g of mesyl chloride and 18.8 g of triethylamine were gradually dropped thereto at 4° C., respectively. The temperature of the solution was allowed to rise to room temperature, and the solution was stirred for an hour. Water was added to stop the reaction, and the solution was extracted with dichloromethane. The organic layer was dried with magnesium sulfate and concentrated, and then purified by silica gel chromatography (hexane/ethyl acetate=10/1), thereby obtaining 9.0 g of 3-methyl-1-nitro-hex-1-ene (yield: 81.4%).

$^1$H-NMR (CDCl$_3$): δ=0.90-0.93 (3H, t, 7.2 Hz), 1.11-1.13 (3H, d, 6.8 Hz), 1.26-1.46 (4H, m), 2.41-4.45 (1H, m), 6.93-6.96 (1H, d, J=13.2 Hz), 7.16-7.22 (1H, dd, J=13.8 Hz, 5.6 Hz).

Example 2-2

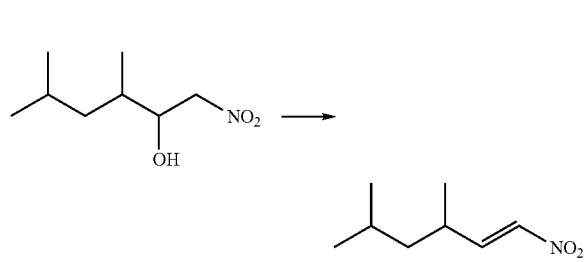

After dissolving 9.0 g of 3,5-dimethyl-1-nitro-2-hexanol in 100 ml of dichloromethane, 6.5 g of mesyl chloride and 10.4 g of triethylamine were gradually dropped thereto at 4° C., respectively. The temperature of the solution was allowed to rise to room temperature, and the solution was stirred for 1.5 hours. Water was added to stop the reaction, and the solution was extracted with dichloromethane. The organic layer was dried with magnesium sulfate and concentrated, and then purified by silica gel chromatography (hexane/ethyl acetate=10/1), thereby obtaining 6.8 g of 3,5-dimethyl-1-nitrohex-1-ene (yield: 83.9%).

$^1$H-NMR (CDCl$_3$): δ=0.89-0.95 (6H, m), 1.10-1.12 (3H, d, J=6.8 Hz), 1.25-1.43 (2H, m), 1.56-1.62 (1H, m), 2.49-2.53 (1H, m), 6.95-6.99 (1H, d, J=13.8 Hz), 7.14-7.20 (1H, dd, J=13.8 Hz, 8.3 Hz).

Example 2-3

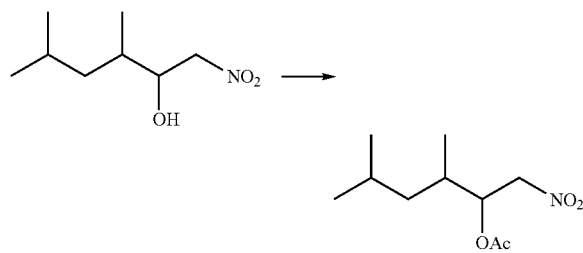

After dissolving 7.8 g of 3,5-dimethyl-1-nitro-2-hexanol in 30 ml of pyridine, 10 ml of acetic anhydride were added thereto, and the solution was stirred at room temperature for 2.5 hours. Ethyl acetate was added to the solution, and the organic layer was washed with 1 mol/l of aqueous hydrochloric acid and saturated saline. The organic layer was dried with magnesium sulfate and concentrated, and then purified by silica gel chromatography (hexane/ethyl acetate=10/1), thereby obtaining 8.4 g of 3,5-dimethyl-1-nitrohex-2-yl acetate (yield: 87.3%).

$^1$H-NMR (CDCl$_3$): δ=0.85-0.95 (9H, m), 1.12-1.28 (2H, m), 1.64-1.67 (2H, m), 2.23 (3H, s), 4.22-4.24 (2H, m), 4.45 (1H, m).

Example 2-4

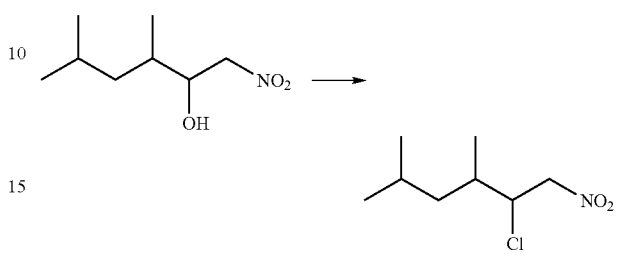

After dissolving 2.0 g of 3,5-dimethyl-1-nitro-2-hexanol in 15 ml of toluene, 4.1 g of thionyl chloride and two drops of N,N-dimethylformamide were added thereto, and the solution was stirred for 2.5 hours at 80° C. The solution was cooled to room temperature and concentrated, and then purified by silica gel chromatography (hexane/ethyl acetate=8/1), thereby obtaining 1.5 g of 2-chloro-3,5-dimethyl-1-nitrohexane (yield: 72.4%).

$^1$H-NMR (CDCl$_3$): δ=0.86-1.36 (9H, m), 1.14-1.17 (2H, m), 1.64-1.68 (2H, m), 4.40-4.42 (1H, m), 4.59-4.61 (2H, m).

Example 3-1

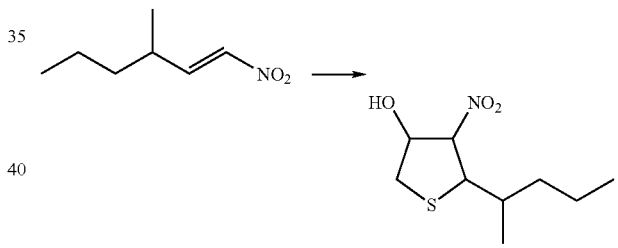

After dissolving 0.30 g of 3-methyl-1-nitrohex-1-ene in 6 ml of ethanol, 0.32 g of triethylamine and 0.16 g of 1,4-dithian-2,5-diol were added thereto, and the solution was heated to 50° C. and stirred for an hour. The solution was cooled to room temperature and diluted with ethyl acetate, and the organic layer was washed with 1 mol/l of aqueous hydrochloric acid and saturated saline, respectively. The organic layer was dried with magnesium sulfate and concentrated, and then purified by silica gel chromatography (hexane/ethyl acetate=8/1), thereby obtaining 0.18 g of 4-nitro-5-(pentan-2-yl)tetrahydrothiophen-3-ol (yield: 42.6%).

$^1$H-NMR (CDCl$_3$): δ=0.87-1.03 (6H, m), 1.22-1.32 (4H, m), 1.64-1.69 (1H, m), 2.85-2.91 (1H, m), 3.08-3.11 (1H, m), 3.30 (1H, Brs), 3.79-3.85 (1H, m), 4.70-4.76 (2H, m).

Example 3-2

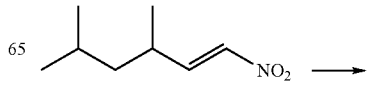

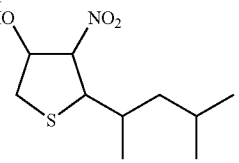

After dissolving 6.8 g of 3,5-dimethyl-1-nitrohex-1-ene in 40 ml of dichloromethane, 6.7 g of triethylamine and 3.6 g of 1,4-dithian-2,5-diol were added thereto, and the solution was stirred for 1.5 hours. The solution was diluted with ethyl acetate, and the organic layer was washed with 1 mol/l of aqueous hydrochloric acid and saturated saline, respectively. The organic layer was dried with magnesium sulfate and concentrated, and then purified by silica gel chromatography (hexane/ethyl acetate=8/1), thereby obtaining 10.9 g of 5-(4-methylpentan-2-yl)-4-nitrotetrahydrothiophen-3-ol (yield: 93.5%)

$^1$H-NMR (CDCl$_3$): δ=0.87-1.01 (6H, m), 1.14-1.28 (5H, m), 1.64-1.72 (2H, m), 2.85-3.12 (3H, m), 4.11-4.31 (1H, m), 4.70-4.83 (2H, m).

Example 3-3

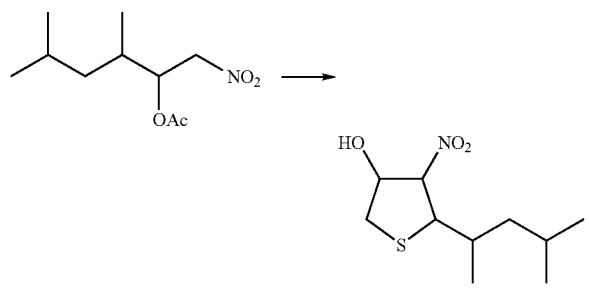

After dissolving 8.4 g of 3,5-dimethyl-1-nitrohex-2-yl acetate in 30 ml of dichloromethane, 7.0 g of triethylamine and 3.7 g of 1,4-dithian-2,5-diol were added thereto at 4° C. After stirring the solution at room temperature for an hour, the solution was washed with saturated saline. Then, the organic layer was dried with magnesium sulfate and concentrated, and then purified by silica gel chromatography (hexane/ethyl acetate=8/1), thereby obtaining 6.6 g of 5-(4-methylpentan-2-yl)-4-nitrotetrahydrothiophen-3-ol (yield: 63.2%).

Example 3-4

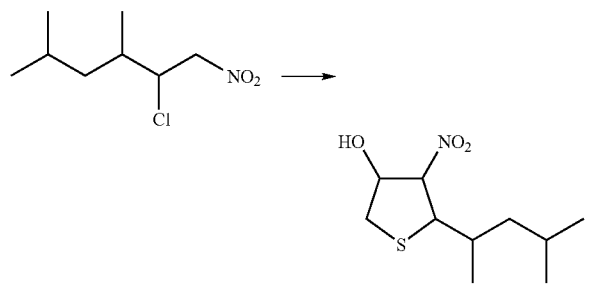

After dissolving 1.5 g of 2-chloro-3,5-dimethyl-1-nitrohexane in 10 ml of toluene, 0.9 g of triethylamine and 0.9 g of 1,4-dithian-2,5-diol were added thereto at 4° C. After stirring the solution at room temperature for 4.5 hours, the solid was filtered out and the filterate was concentrated. The solution was purified by silica gel chromatography (hexane/ethyl acetate=8/1), thereby obtaining 0.7 g of 5-(4-methylpentan-2-yl)-4-nitrotetrahydrothiophen-3-ol (yield: 39.3%).

Example 4-1

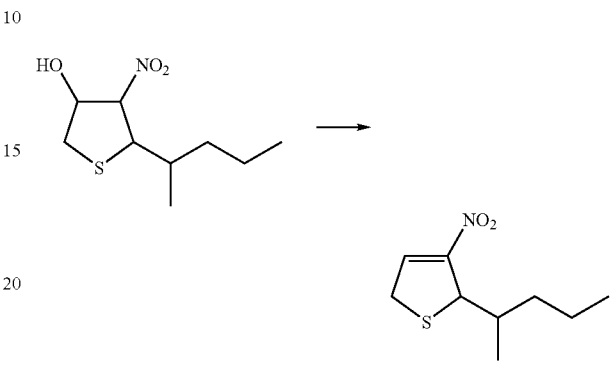

After dissolving 150 mg of 4-nitro-5-(pentan-2-yl)tetrahydrothiophen-3-ol in 4 ml of dichloromethane, 86 mg of mesyl chloride and 138 mg of triethylamine were gradually dropped thereto at 4° C. The temperature of the solution was allowed to rise to room temperature, and the solution was stirred for 3.5 hours. Water was added to stop the reaction, and the solution was extracted with dichloromethane. The organic layer was dried with magnesium sulfate and concentrated, and then purified by silica gel chromatography (hexane/ethyl acetate=10/1), thereby obtaining 78 mg of 3-nitro-2-(pentan-2-yl)-2,5-dihydrothiophene (yield: 57.3%).

$^1$H-NMR (CDCl$_3$): δ=0.84-0.98 (6H, m), 1.17-1.40 (4H, m), 2.10-2.25 (1H, m), 3.76-3.80 (2H, m), 4.60-4.75 (1H, m), 7.22-7.24 (1H, m).

Example 4-2

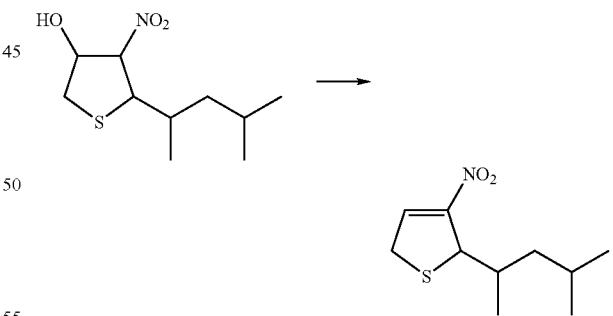

After dissolving 0.50 g of 5-(4-methylpentan-2-yl)-4-nitrotetrahydrothiophen-3-ol in 4 ml of dichloromethane, 0.27 g of mesyl chloride and 0.33 g of triethylamine were gradually dropped thereto at 4° C. The temperature of the solution was allowed to rise to room temperature, and the solution was stirred for 7.5 hours. Water was added to stop the reaction, and the solution was extracted with dichloromethane. The organic layer was dried with magnesium sulfate and concentrated, and then purified by silica gel chromatography (hexane/ethyl acetate=10/1), thereby obtaining 0.22 g of 2-(4-methylpentan-2-yl)-3-nitro-2,5-dihydrothiophene (yield: 47.7%).

¹H-NMR (CDCl₃): δ=0.87-1.00 (6H, m), 1.15-1.30 (5H, m), 1.64-1.72 (2H, m), 3.75-3.79 (2H, m), 4.60-4.74 (1H, m), 7.21-7.24 (1H, m).

Example 4-3

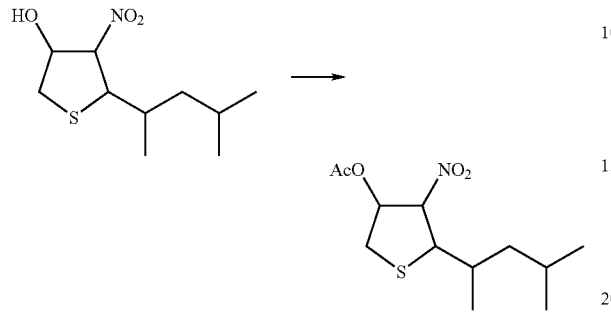

After dissolving 1.00 g of 5-(4-methylpentan-2-yl)-4-nitrotetrahydrothiophen-3-ol in 10 ml of toluene, 0.7 g of pyridine and 1.4 g of acetic anhydride were added thereto. The solution was stirred at room temperature for 2 hours. Water was added to stop the reaction, and the organic layer was washed with 1 mol/l of aqueous hydrochloric acid and saturated saline. The organic layer was dried with magnesium sulfate and concentrated, and then purified by silica gel chromatography (hexane/ethyl acetate=9/1), thereby obtaining 1.10 g of 5-(4-methylpentan-2-yl)-3-nitrotetrahydrothiophen-3-yl acetate (yield: 94.8%).

¹H-NMR (CDCl₃): δ=0.87-1.01 (6H, m), 1.14-1.28 (5H, m), 1.64-1.72 (2H, m), 2.41 (3H, s), 2.85-3.12 (3H, m), 4.11-4.31 (1H, m), 4.70-4.83 (2H, m).

Example 5-1

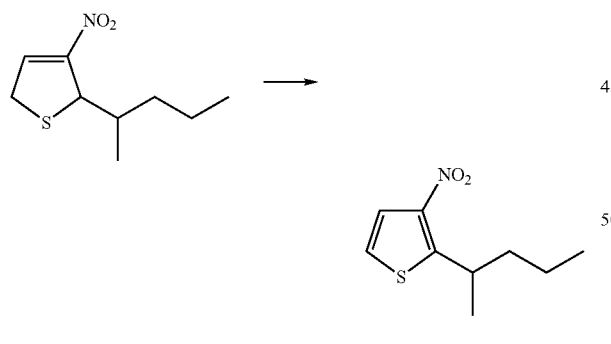

After dissolving 78 mg of 3-nitro-2-(pentan-2-yl)-2,5-dihydrothiophene in 2 ml of dichloromethane, a solution prepared by dissolving 78 mg of sulfuryl chloride in 2 ml of dichloromethane was added thereto, and the solution was stirred at room temperature for 2.5 hours. After adding an aqueous solution of saturated sodium bicarbonate, the solution was extracted with dichloromethane. The organic layer was washed with saturated saline, dried with magnesium sulfate and concentrated, and then purified by NH-silica gel chromatography (hexane/ethyl acetate=10/1), thereby obtaining 69 mg of 3-nitro-2-(pentan-2-yl)thiophene (yield: 88.7%).

¹H-NMR (CDCl₃): δ=0.90-0.93 (3H, m), 1.30-1.42 (5H, m), 1.60-1.70 (2H, m), 4.01-4.07 (1H, m), 7.01-7.10 (1H, d, J=5.9 Hz), 7.53-7.55 (1H, d, J=5.4 Hz).

Example 5-2

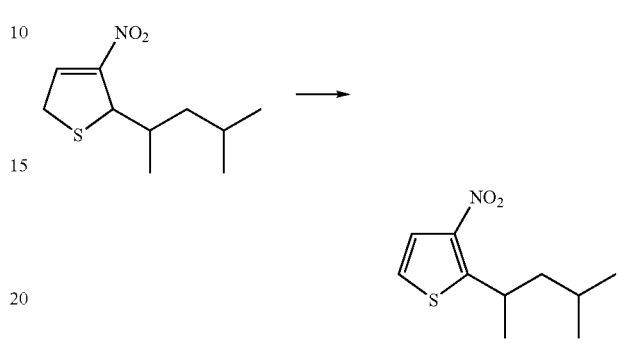

After dissolving 2.8 g of 2-(4-methylpentan-2-yl)-3-nitro-2,5-dihydrothiophene in 40 ml of dichloromethane, a solution prepared by dissolving 2.6 g of sulfuryl chloride in 5 ml of dichloromethane was added thereto, and the solution was stirred at room temperature for 1.5 hours. After adding an aqueous solution of saturated sodium bicarbonate, the solution was extracted with dichloromethane. The organic layer was washed with saturated saline, dried with magnesium sulfate and concentrated, and then purified by NH-silica gel chromatography (hexane/ethyl acetate=10/1), thereby obtaining 2.0 g of 2-(4-methylpentan-2-yl)-3-nitrothiophene (yield: 70.1%).

¹H-NMR (CDCl₃): δ=0.80-0.96 (6H, m), 1.30-1.34 (3H, m), 1.44-1.64 (2H, m), 3.06-3.08 (1H, m), 4.12-4.14 (1H, m), 7.09-7.10 (1H, d, J=5.4 Hz), 7.53-7.54 (1H, d, J=5.9 Hz).

Example 5-3

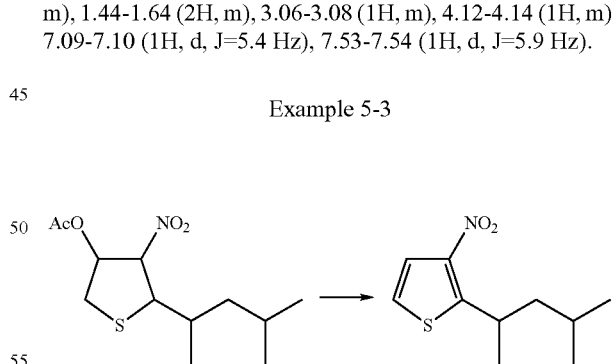

After dissolving 1.1 g of 5-(4-methylpentan-2-yl)-4-nitrotetrahydrothiophen-3-yl acetate in 7 ml of toluene, the solution was cooled to 4° C. A solution prepared by dissolving 0.8 g of sulfuryl chloride in 2 ml of toluene was added thereto. The temperature of the solution was allowed to rise room temperature, and the solution was stirred for 2 hours. Water was added to stop reaction, and the organic layer was washed with 1 mol/l aqueous sodium hydroxide and saturated saline. The organic layer was dried with magnesium sulfate and concentrated, and then purified by silica gel chromatography (hexane/ethyl acetate=10/1), thereby obtaining 0.8 g of 2-(4-methylpentan-2-yl)-3-nitrothiophene (yield: 85.0%).

Example 6

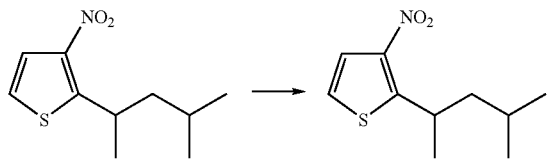

After dissolving 0.33 g of 2-(4-methylpentan-2-yl)-3-nitrothiophene in 6 ml of ethanol, 0.88 g of tin chloride (II) and 0.97 g of concentrated hydrochloric acid were added thereto, and the reaction solution was heated to 70° C. and stirred for an hour. After cooling the solution to room temperature, 1 mol/l of an aqueous sodium hydroxide was added thereto, and the solution stirred for five minutes. The resultant was filtered on cellite, and the filterate was extracted with ethyl acetate. The organic layer was washed with 1 mol/l of aqueous sodium hydroxide and saturated saline. Then, the organic layer was dried with magnesium sulfate and concentrated, and then purified by silica gel chromatography (hexane/ethyl acetate=8/1), thereby obtaining 0.11 g of 2-(4-methylpentan-2-yl)-3-aminothiophene (yield: 39.0%).

$^1$H-NMR (CDCl$_3$): δ=0.83-0.98 (6H, m), 1.19-1.60 (5H, m), 2.93-2.95 (1H, m), 3.38 (1H, Brs), 6.41-6.55 (1H, dd, J=4.9 Hz, 5.4 Hz), 6.93-7.04 (1H, dd, J=4.9 Hz, 5.4 Hz).

According to the invention, a 2-alkyl-3-aminothiophene derivative, which is an effective production intermediate in the field of medicines and agrochemicals, can be provided by an efficient method. Moreover, the invention has a great deal of potential in industrial use due to its advantageous capability of industrial production.

What is claimed is:
1. A method of producing a 2-alkyl-3-aminothiophene derivative represented by Formula (4), the method comprising (A) oxidizing a compound represented by Formula (1) to produce a compound represented by Formula (3), and (B) reducing the compound represented by Formula (3):

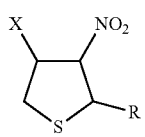 (1)

wherein, in Formula (1), R represents a substituent represented by the following Formula (6):

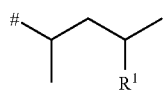 (6)

wherein, in Formula (6), R$^1$ represents a hydrogen atom, or a straight-chain or branched alkyl group having 1 to 6 carbon atoms and # represents a site of bonding with the compound represented by Formula (1); and X represents a hydroxy group, a halogen atom or a substituent represented by the following Formula (2):

$$\#\text{-}O\text{-}A(O)_n\text{-}Q \quad (2)$$

wherein, in Formula (2), A represents a carbon atom or a sulfur atom; n is 1 when A is a carbon atom, and is 1 or 2 when A is a sulfur atom; Q represents an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms; and # represents a site of bonding with the compound represented by Formula (1):

 (3)

wherein, in Formula (3), R is the same as in Formula (1):

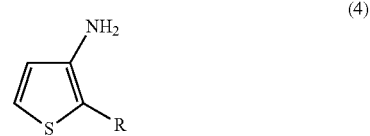 (4)

wherein, in Formula (4), R is the same as in Formula (1).
2. The method according to claim 1, wherein R represents a 1,3-dimethylbutyl group.
3. The method according to claim 1, wherein the compound represented by Formula (1) is a compound represented by Formula (8), and the method further comprises producing a compound represented by Formula (1a) from a compound represented by the following Formula (8):

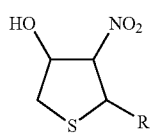 (8)

wherein, in Formula (8), R is the same as in Formula (1):

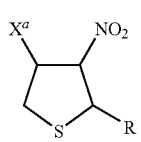 (1a)

wherein, in Formula (1a), R is the same as in Formula (1) and X$^a$ represents a halogen atom or the substituent represented by Formula (2).
4. The method according to claim 1, wherein (A) further comprises (A-1) producing a compound represented by Formula (5) from the compound represented by Formula (1), and (A-2) producing the compound represented by Formula (3) from the compound represented by Formula (5):

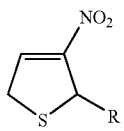
(5)

wherein, in Formula (5), R is the same as in Formula (1).

5. The method according to claim 1, wherein the compound represented by Formula (1) is a compound represented by Formula (8), and wherein the method further comprises reacting a compound represented by Formula (7) with α-mercaptoacetaldehyde or 1,4-dithian-2,5-diol to produce a compound represented by Formula (8):

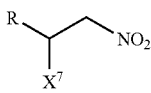
(7)

wherein, in Formula (7), R is the same as in Formula (1) and $X^7$ represents a halogen atom or a substituent represented by Formula (2):

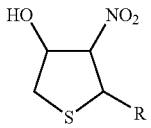
(8)

wherein, in Formula (8), R is the same as in Formula (1).

6. The method according to claim 5, wherein the method further comprises producing the compound represented by Formula (7) from a compound represented by the following Formula (9):

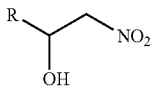
(9)

wherein, in Formula (9), R is the same as in Formula (1).

7. The method according to claim 6, wherein the method further comprises reacting a compound represented by Formula (10) with nitromethane to produce the compound represented by Formula (9):

(10)

wherein, in Formula (10), R is the same as in Formula (1).

8. The method according to claim 1, wherein the compound represented by Formula (1) is a compound represented by Formula (8), and wherein the method further comprises reacting a compound represented by Formula (11) with α-mercaptoacetaldehyde or 1,4-dithian-2,5-diol to produce a compound represented by Formula (8):

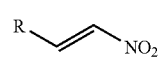
(11)

wherein, in Formula (11), R is the same as in Formula (1):

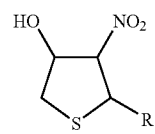
(8)

wherein, in Formula (8), R is the same as in Formula (1).

9. The method according to claim 8, wherein the method further comprises dehydrating a compound represented by Formula (9) to produce the compound represented by Formula (11):

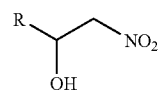
(9)

wherein, in Formula (9), R is the same as in Formula (1).

10. The method according to claim 9, wherein the method further comprises reacting a compound represented by Formula (10) with nitromethane to produce the compound represented by Formula (9):

(10)

wherein, in Formula (10), R is the same as in Formula (1).

11. A 3-nitrotetrahydrothiophene derivative represented by the following Formula (1):

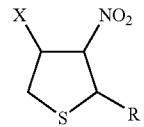
(1)

wherein, in Formula (1), R represents a substituent represented by the following Formula (6):

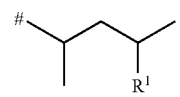
(6)

wherein, in Formula (6), $R^1$ represents a hydrogen atom, or a straight-chain or branched alkyl group having 1 to 6 carbon atoms and # represents a site of bonding with the 3-nitrotetrahydrothiophene derivative; and X represents a hydroxy group, a halogen atom, or a substituent represented by the following Formula (2):

  (2)

wherein, in Formula (2), A represents a carbon atom or a sulfur atom; n is a 1 when A is a carbon atom, and is 1 or 2 when A is a sulfur atom; and Q represents an alkyl group having 1 to 10 carbon atoms, a cycloalkyl group having 3 to 10 carbon atoms, a haloalkyl group having 1 to 10 carbon atoms, a hydrocarbyloxy group having 1 to 10 carbon atoms, or an aryl group that may be substituted by an alkyl group having 1 to 6 carbon atoms.

12. The 3-nitrotetrahydrothiophene derivative according, to claim 11, wherein R in Formula (1) represents a 1,3-dimethylbutyl group.

13. The 3-nitrotetrahydrothiophene derivative according to claim 11, wherein X in Formula (1) represents a hydroxy group.

14. The 3-nitrotetrahydrothiophene derivative according to claim 13, wherein R in Formula (1) represents a 1,3-dimethylbutyl group.

15. A 3-nitro-2,5-dihydrothiophene derivative represented by the following Formula (5):

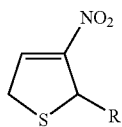  (5)

wherein, in Formula (5), R represents an alkyl group having 1 to 18 carbon atoms that may be substituted by an alkyl group having 1 to 10 carbon atoms or by a cycloalkyl group having 3 to 10 carbon atoms, a cycloalkyl group having 3 to 10 carbon atoms that may be substituted by an alkyl group having 1 to 10 carbon atoms or by a cycloalkyl group having 3 to 10 carbon atoms, or a bicycloalkyl group having 6 to 12 carbon atoms that may be substituted by an alkyl group having 1 to 10 carbon atoms or by a cycloalkyl group having 3 to 10 carbon atoms.

16. The 3-nitro-2,5-dihydrothiophene derivative according to claim 15, wherein R in Formula (5) represents a substituent represented by the following Formula (6):

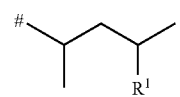  (6)

wherein, in Formula (6), $R^1$ represents a hydrogen atom, or a straight-chain or branched alkyl group having 1 to 6 carbon atoms and # represents a site of bonding with the 3-nitro-2,5-dihydrothiophene derivative.

17. The 3-nitro-2,5-dihydrothiophene derivative according to claim 15, wherein R in Formula (5) represents a 1,3-dimethylbutyl group.

18. A 2-alkyl-3-nitrothiophene derivative represented by the following Formula (3):

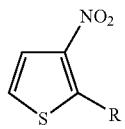  (3)

wherein, in Formula (3), R represents a substituent represented by the following Formula (6):

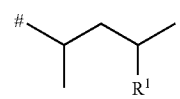  (6)

wherein, in Formula (6), $R^1$ represents a hydrogen atom, or a straight-chain or branched alkyl group having 1 to 6 carbon atoms, and # represents a site of bonding with the 2-alkyl-3-nitrothiophene derivative.

19. The 2-alkyl-3-nitrothiophene derivative according to claim 18, wherein R in Formula (3) represents a 1,3-dimethylbutyl group.

* * * * *